(12) United States Patent
Kim et al.

(10) Patent No.: US 11,479,796 B2
(45) Date of Patent: Oct. 25, 2022

(54) METHOD FOR PRODUCTION OF SUGAR ALCOHOL FROM RED ALGAE

(71) Applicant: Korea University Research and Business Foundation, Seoul (KR)

(72) Inventors: Kyoung Heon Kim, Seoul (KR); Dong Hyun Kim, Busan (KR); Eun-Ju Yun, Seoul (KR)

(73) Assignee: Korea Univercity Research and Business Foundation, Seoul (KR)

( * ) Notice: Subject to any disclaimer, the term of this patent is extended or adjusted under 35 U.S.C. 154(b) by 0 days.

(21) Appl. No.: 17/273,886

(22) PCT Filed: Sep. 5, 2019

(86) PCT No.: PCT/KR2019/011509
§ 371 (c)(1),
(2) Date: Mar. 5, 2021

(87) PCT Pub. No.: WO2020/050663
PCT Pub. Date: Mar. 12, 2020

(65) Prior Publication Data
US 2021/0317492 A1    Oct. 14, 2021

(30) Foreign Application Priority Data
Sep. 6, 2018 (KR) .................. 10-2018-0106552

(51) Int. Cl.
| | | |
|---|---|---|
| *C12P 19/02* | (2006.01) | |
| *C07H 1/00* | (2006.01) | |
| *C07H 17/04* | (2006.01) | |
| *C12P 17/04* | (2006.01) | |

(52) U.S. Cl.
CPC ............... *C12P 19/02* (2013.01); *C07H 1/00* (2013.01); *C07H 17/04* (2013.01); *C12P 17/04* (2013.01); *C12Y 302/01081* (2013.01)

(58) Field of Classification Search
CPC .. C12Y 302/01081; C07H 1/00; C07H 17/04; C07D 307/20; C12P 19/02; C12P 17/04; C12P 7/22
See application file for complete search history.

(56) References Cited

U.S. PATENT DOCUMENTS 9,902,983 B2 *  2/2018  Kim ............... C12Y 302/01082

FOREIGN PATENT DOCUMENTS

| KR | 10-1864800 B1 | 6/2018 | |
|---|---|---|---|
| KR | 10-1864800_MT | * 6/2018 | ............... C12P 19/12 |

OTHER PUBLICATIONS

Hehemann et al., Bacteria of the human gut microbiome catabolize red seaweed glycans with carbohydrate-active enzyme updates from extrinsic microbes. PNAS, 2012, vol. 109(48): 19786-19791. (Year: 2012).*

Lahaye M., Chemistry and physico-chemistry of phycocolloids. Cah. Biol. Mar., 2001, vol. 42 : 137-157. (Year: 2001).*

Young KS., An Enzymatic and Chemical Study of AGAR . 1972, PhD Thesis, Department of Microbiology and Immunology, McGill University, Montreal, Canada, pp. 1-201. (Year: 1972).*

Hee Taek Kim et al., "The complete enzymatic saccharification of agarose and its application to simultaneous saccharification and fermentation of agarose for ethanol production", Bioresource Technology, 2012, pp. 301-306, vol. 107.

Hee Taek Kim et al., "High temperature and low acid pretreatment and agarase treatment of agarose for the production of sugar and ethanol from red seaweed biomass", Bioresource Technology, 2013, pp. 582-587, vol. 136.

Chan Hyoung Lee et al., "A Novel Agarolytic ß-Galactosidase Acts on Agarooligosaccharides for Complete Hydrolysis of Agarose into Monomers", Applied and Environmental Microbiology, Oct. 2014, pp. 5965-5973, vol. 80, No. 19.

Chan Hyoung Lee et al., "Saccharification of agar using hydrothermal pretreatment and enzymes supplemented with agarolytic ß-galactosidase", Process Biochemistry, 2015, pp. 1629-1633, vol. 50.

M. Abdel-Akher et al., "Reduction of Sugars with Sodium Borohydride", J. Am. Chem. Soc., 1951, pp. 4691-4692, vol. 73, No. 10.

Eun Ju Yun et al., "Production of 3,6-anhydro-l-galactose from agarose by agarolytic enzymes of Saccharophagus degradans 2-40", Process Biochemistry, 2011, pp. 88-93, vol. 46.

Jan-Hendrik Hehemann et al., "Bacteria of the human gut microbiome catabolize red seaweed glycans with carbohydrate-active enzyme updates from extrinsic microbes", PNAS, Nov. 27, 2012, pp. 19786-19791, vol. 109, No. 48.

NCBI, GenBank accession No. WP_007560915.1, beta-agarase [Bacteroides plebeius], Mar. 22, 2015, 1 pg.

NCBI, GenBank accession No. ABD81904.1, b-agarase [Saccharophagus degradans 2-40], Feb. 10, 2014, 2 pgs.

NCBI, GenBank accesssion No. WP_011469134.1, glycosyhydrolase [Saccharophagus degradans], May 24, 2013, 1 pg.

International Search Report for PCT/KR2019/011509 dated Jan. 10, 2020 (PCT/ISA/210).

* cited by examiner

*Primary Examiner* — Ganapathirama Raghu
(74) *Attorney, Agent, or Firm* — Sughrue Mion, PLLC

(57) ABSTRACT

The present invention relates to a method for chemical production of 3,6-anhydro-L-galactitol (L-AHGol), which is a novel sugar alcohol, and agarobititol (ABol), which is a disaccharide having the same agarobititol as a reductant end thereof, from sea algae.

3 Claims, 13 Drawing Sheets

Specification includes a Sequence Listing.

[FIG 1A]
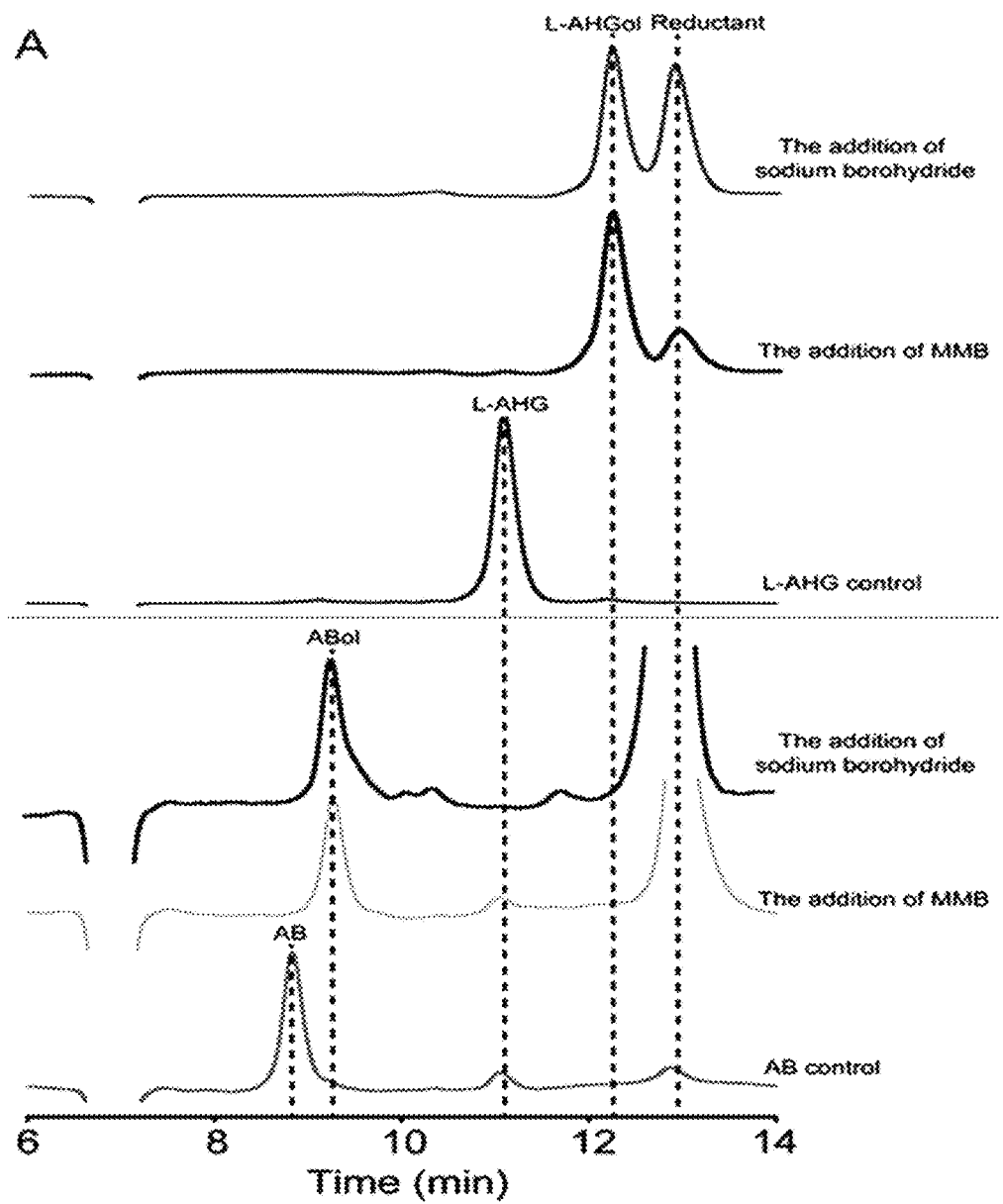

[FIG 1B]
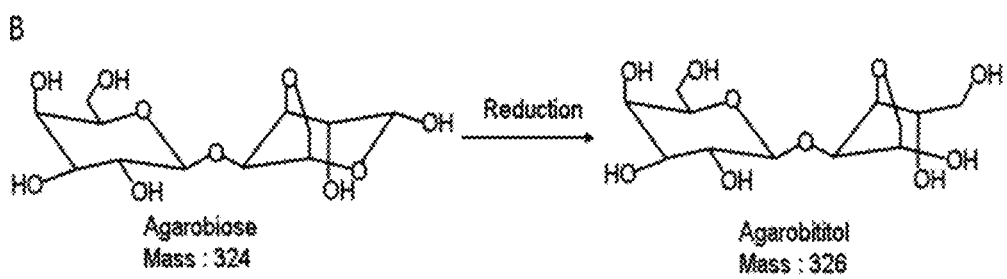
[FIG 1C]
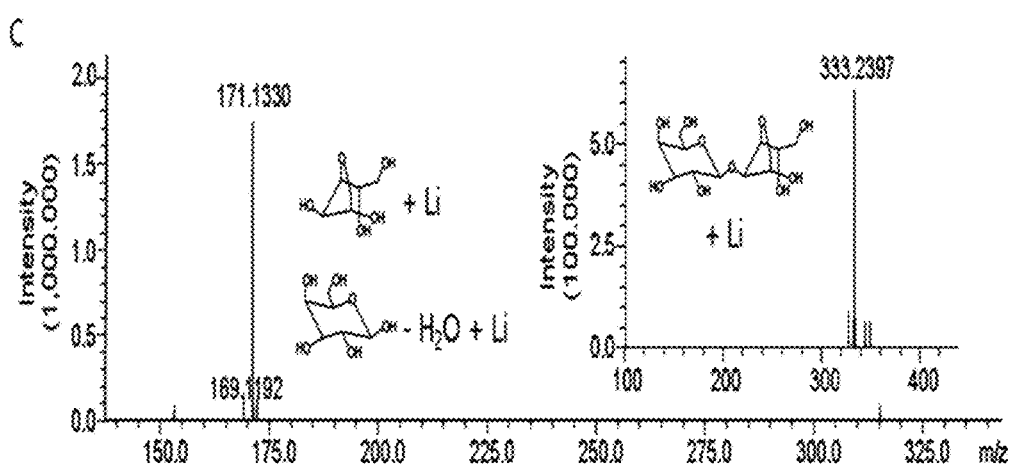
[FIG 1D]
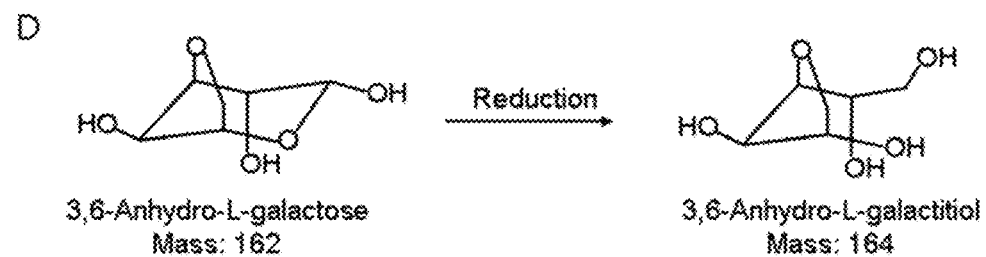

[FIG 1E]
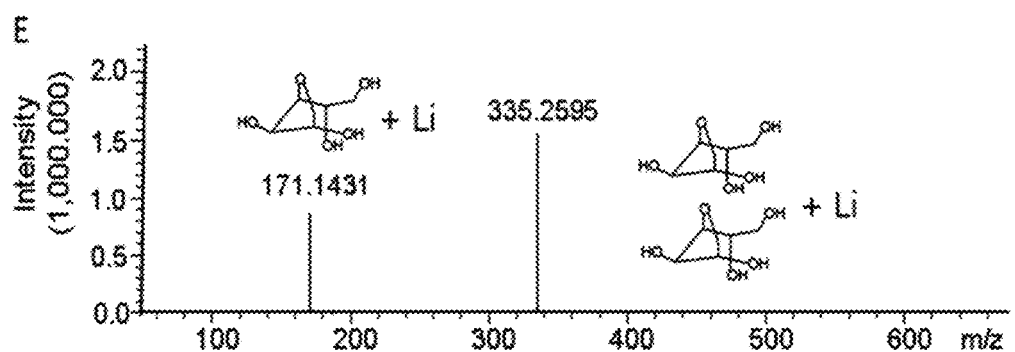

[FIG 2]
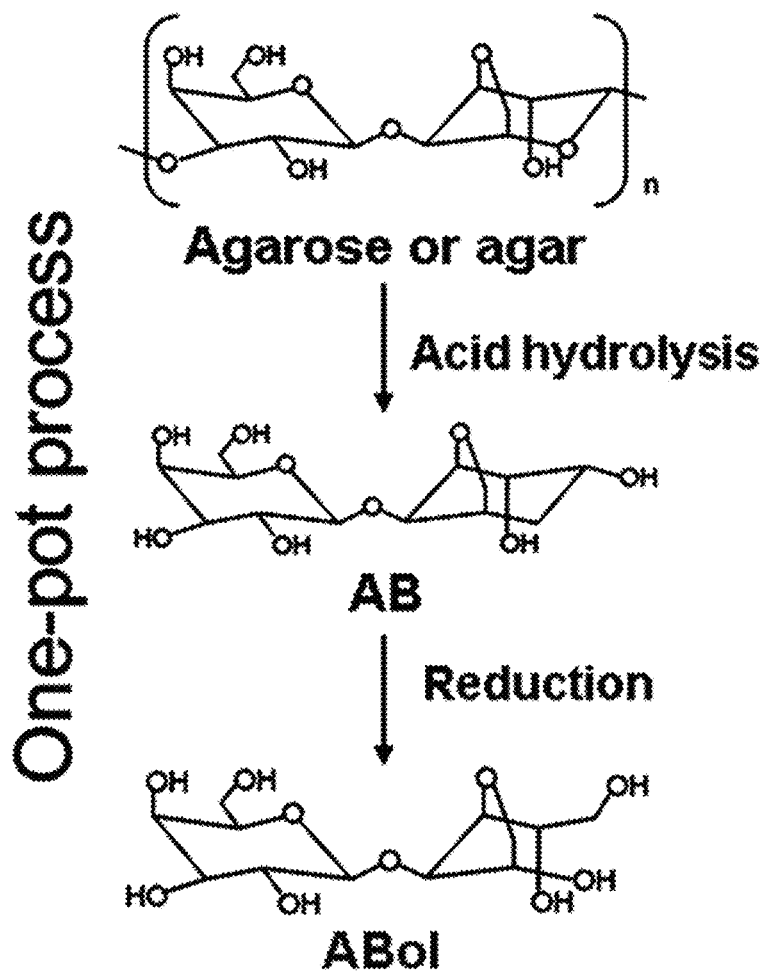

[FIG 3A]
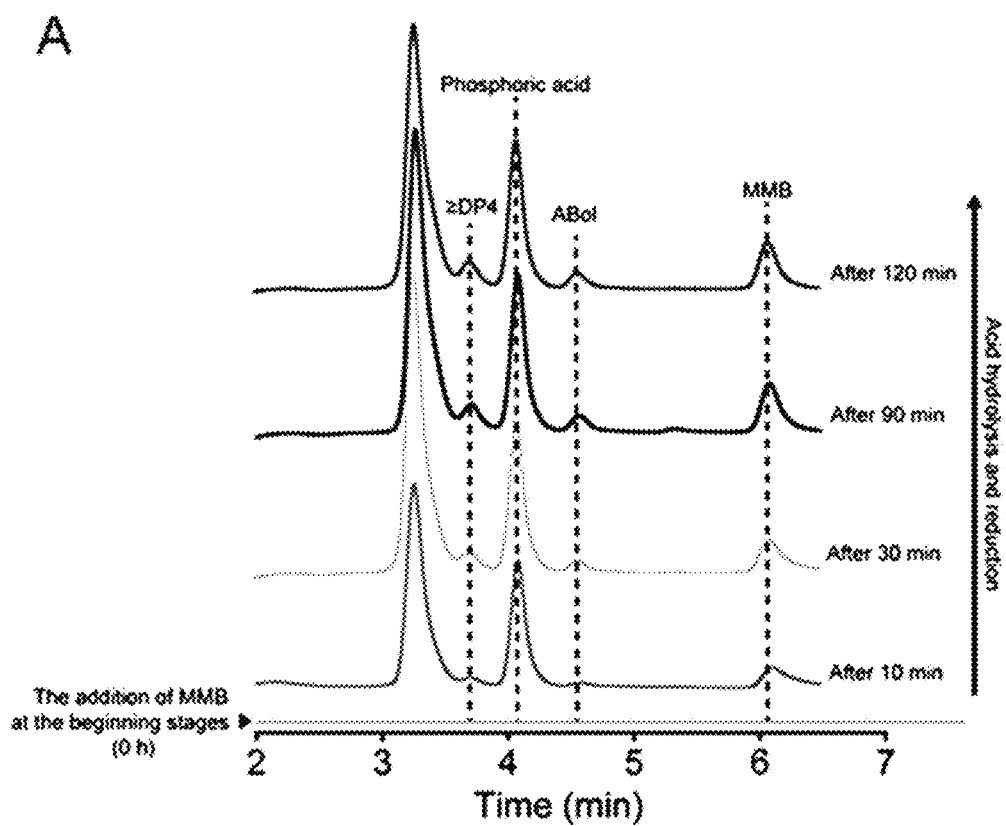

[FIG 3B]
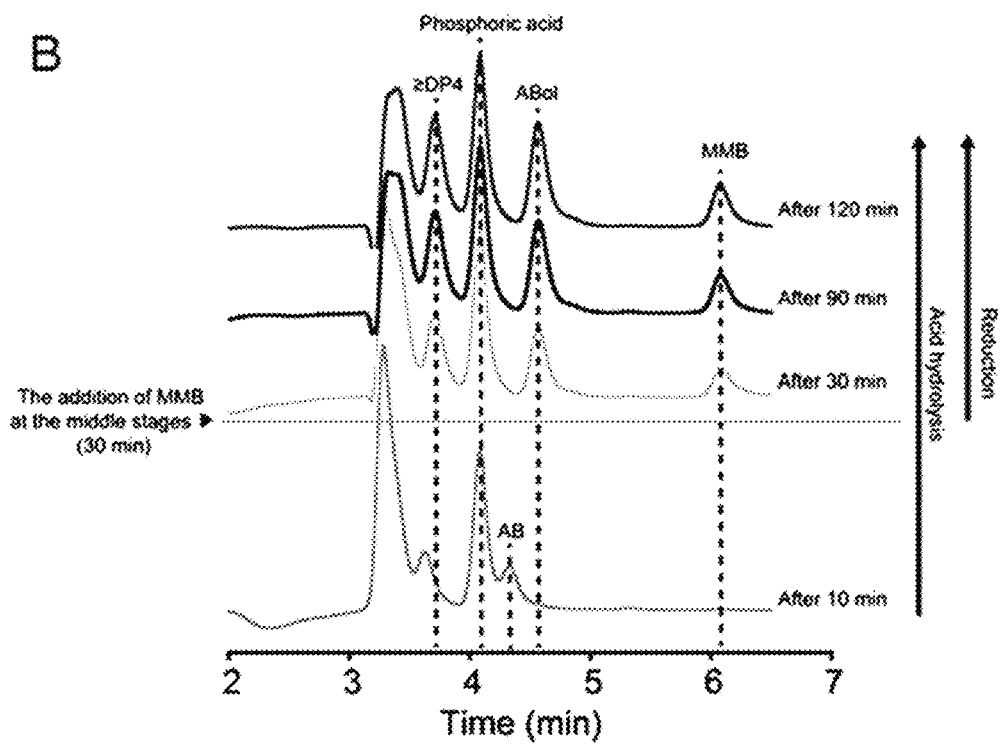

[FIG 3C]
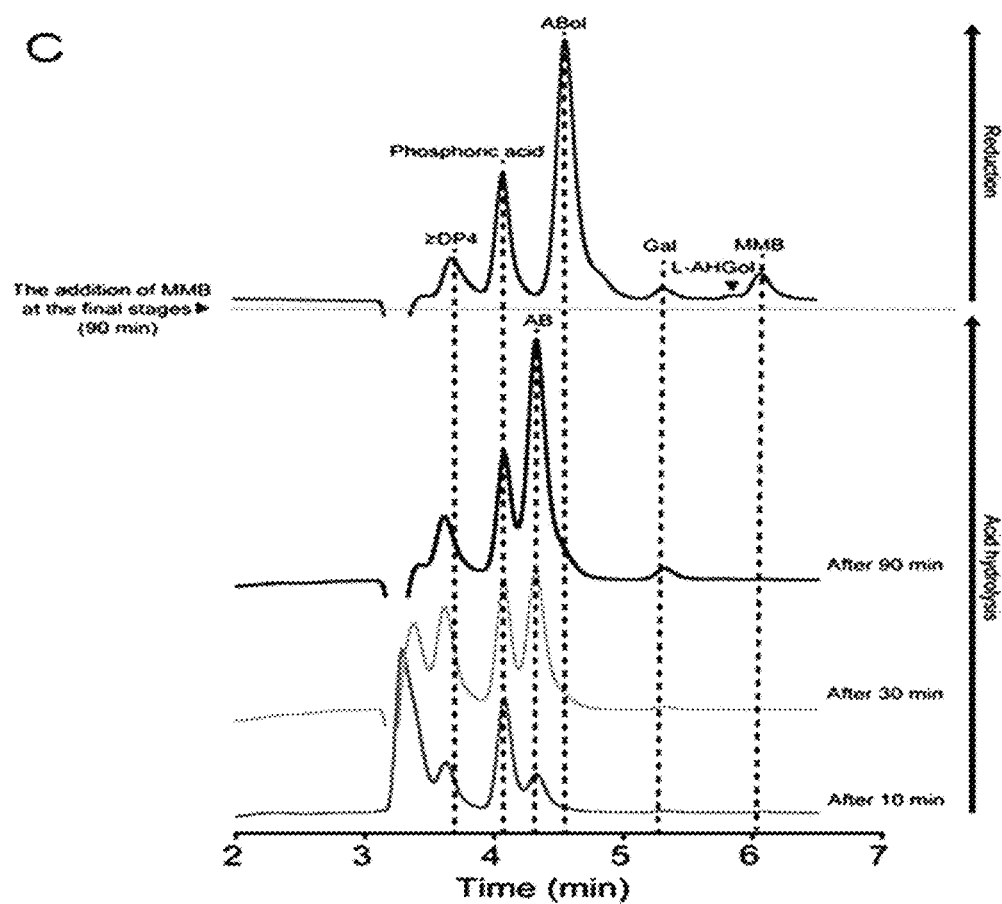

[FIG 3D]
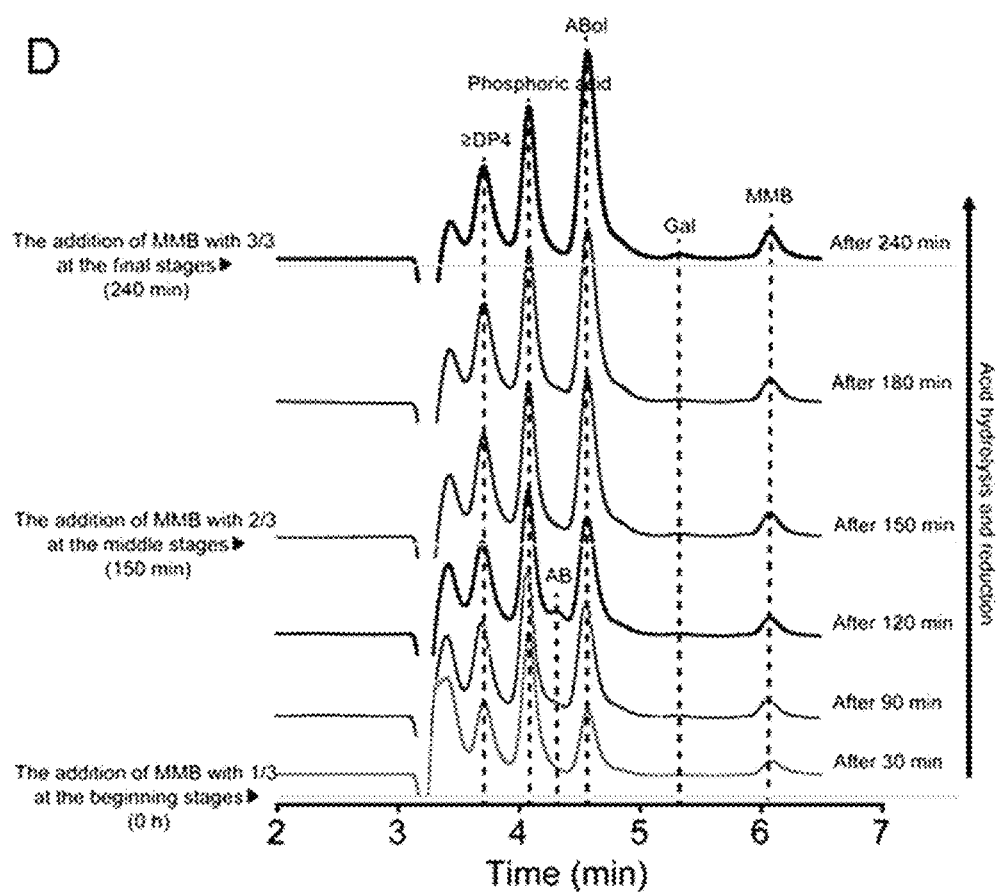

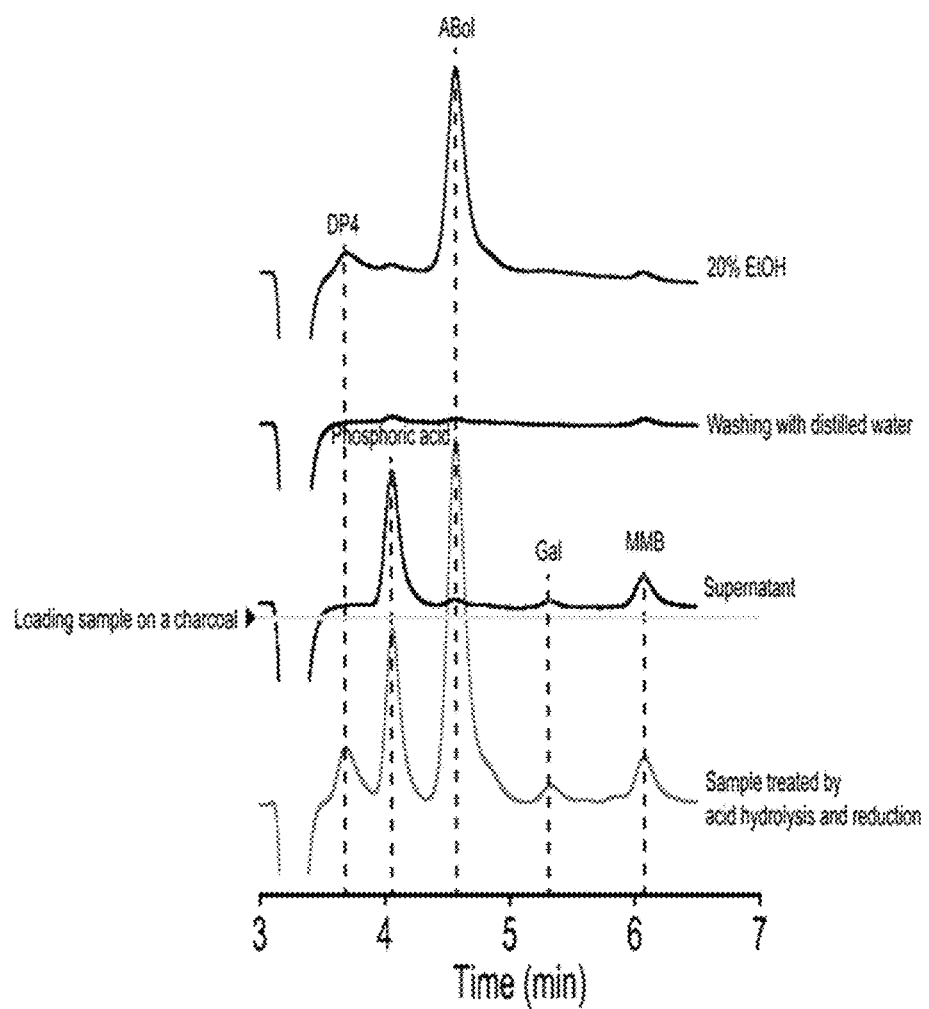
[FIG 4]

[FIG 5]
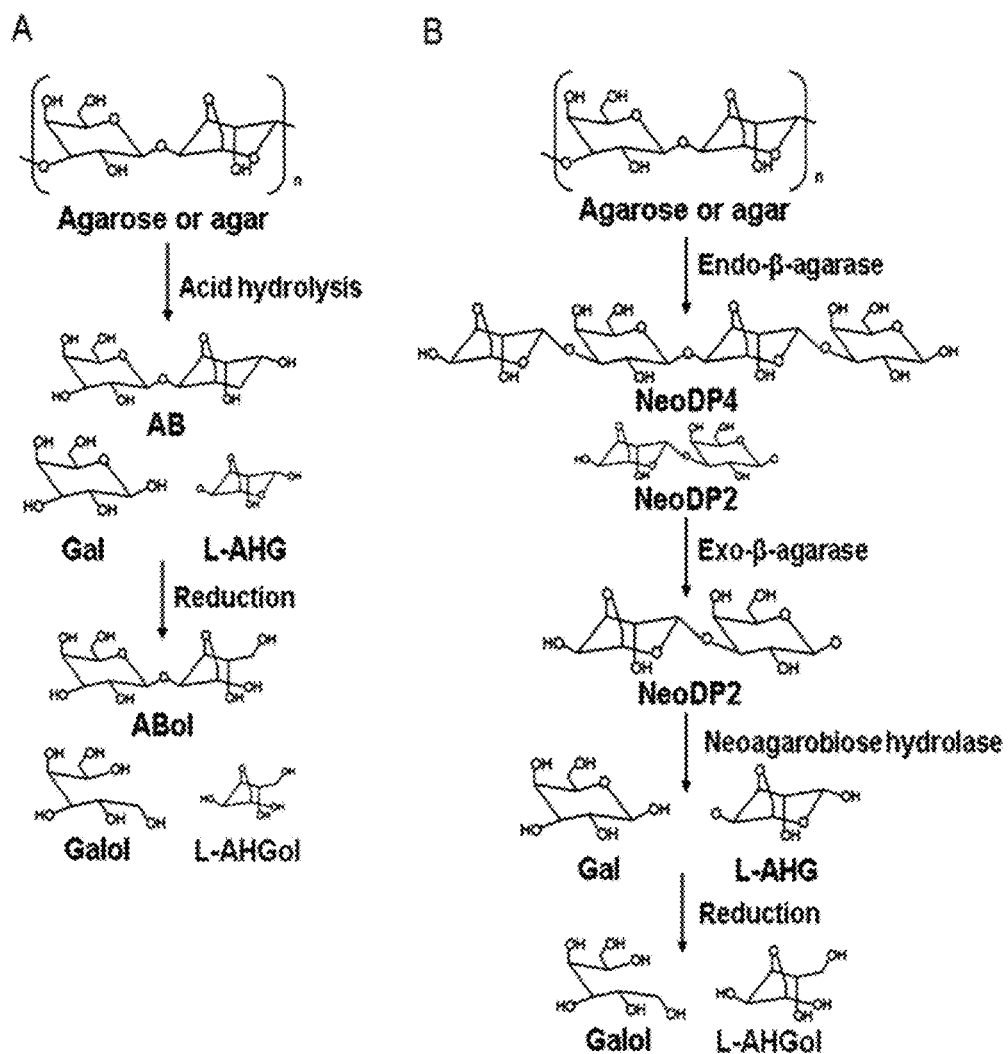

[FIG 6A]
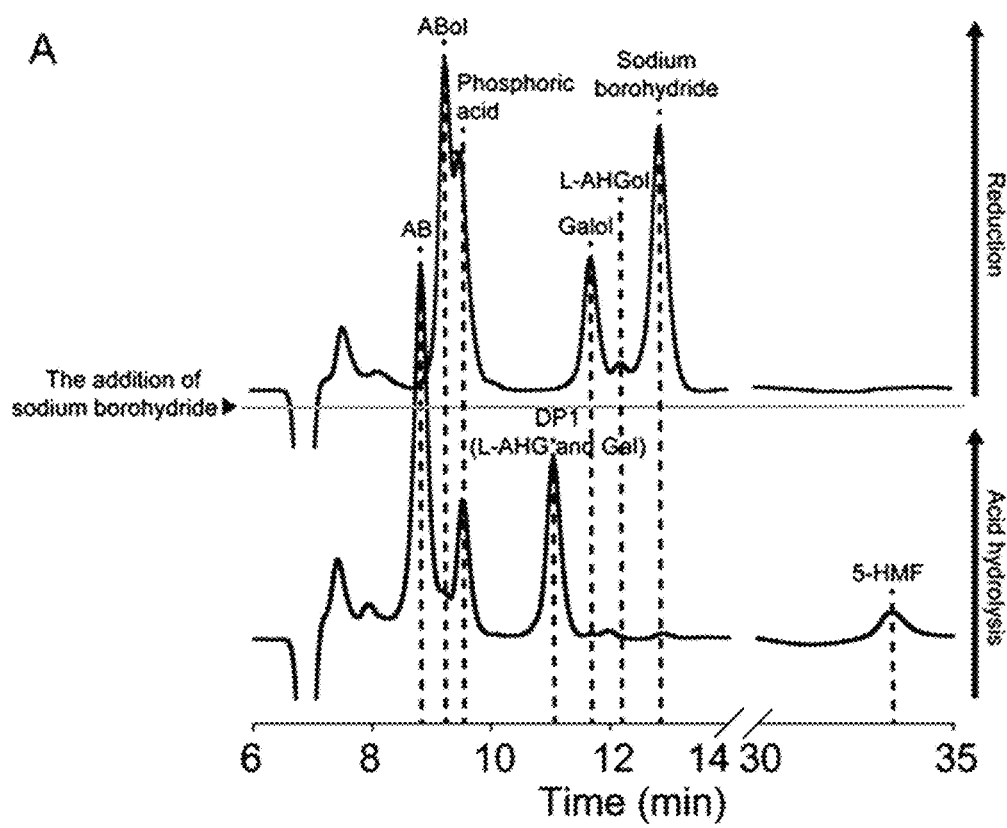

L-AHG▶

NeoDP2▶
D-Gal▶
NeoDP4▶
NeoDP6▶

STD  1 2 3 4

All reactions were performed sequentially.
1. Agarose
2. BpGH16A reaction products
3. Aga50D reaction products
4. SdNABH reaction products

[FIG 6C]
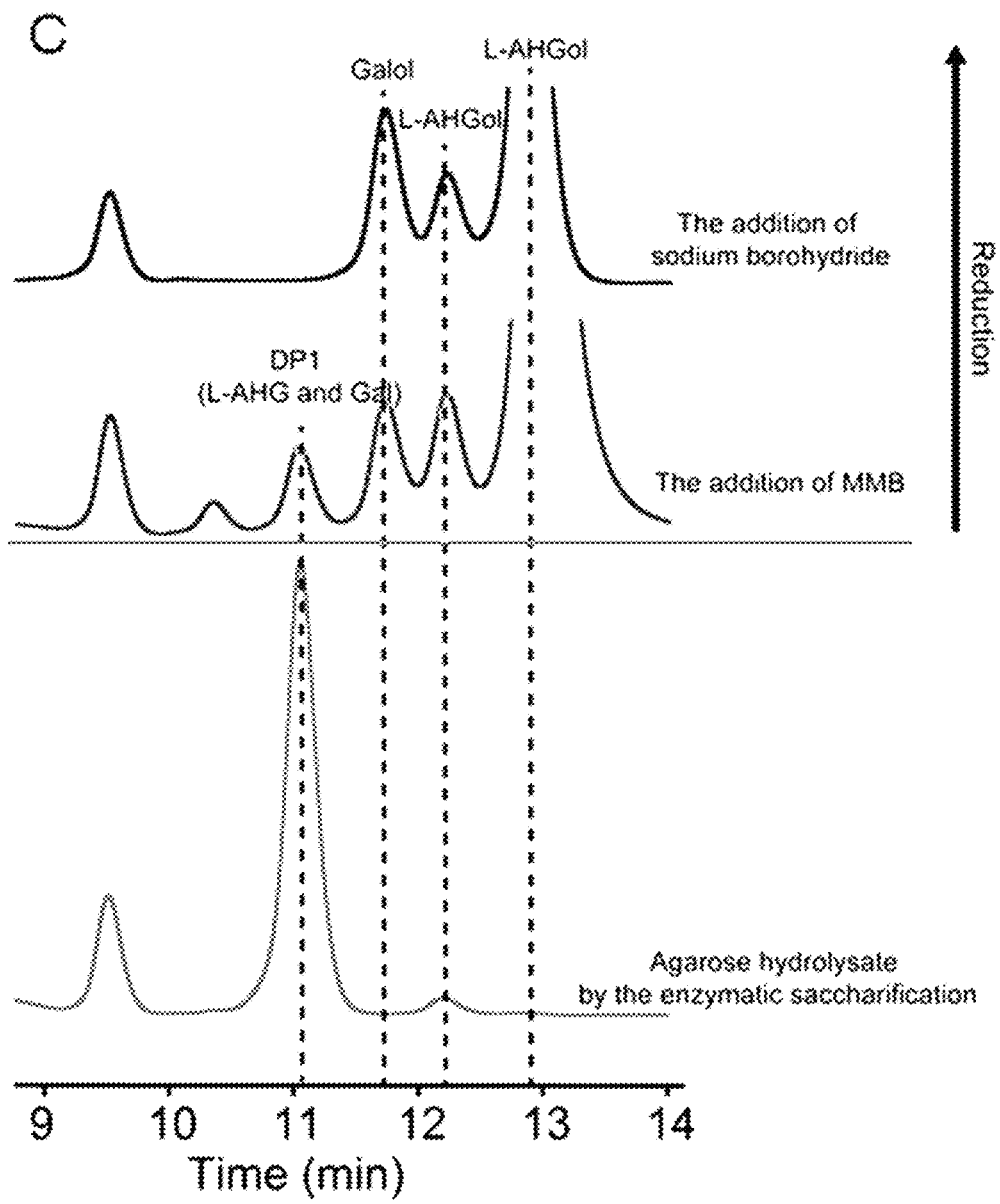

SEQUENCE LISTING

```
<160> NUMBER OF SEQ ID NOS: 6

<210> SEQ ID NO 1
<211> LENGTH: 316
<212> TYPE: PRT
<213> ORGANISM: Unknown
<220> FEATURE:
<223> OTHER INFORMATION: Saccharophagus degradans endo-beta-agarase
      BpGH16A

<400> SEQUENCE: 1

Met Lys Arg Lys Leu Phe Thr Ile Cys Leu Ala Ser Leu Gln Phe Ala
1               5                   10                  15

Cys Ala Ala Glu Asn Leu Asn Asn Lys Ser Tyr Glu Trp Asp Ile Tyr
            20                  25                  30

Pro Val Pro Ala Asn Ala Gly Asp Gly Met Val Trp Lys Leu His Pro
        35                  40                  45

Gln Ser Asp Asp Phe Asn Tyr Ile Ala Asp Glu Lys Asp Lys Gly Lys
    50                  55                  60

Glu Phe Tyr Ala Lys Trp Thr Asp Phe Tyr His Asn His Trp Thr Gly
65                  70                  75                  80

Pro Ala Pro Thr Ile Trp Gln Arg Asp His Val Ser Val Ser Asp Gly
                85                  90                  95

Phe Leu Lys Ile Arg Ala Ser Arg Pro Glu Asp Val Pro Leu Lys Lys
            100                 105                 110
```

```
Val Val Ser Gly Pro Asn Thr Lys Glu Leu Pro Gly Thr Tyr Thr Gly
            115                 120                 125

Cys Ile Thr Ser Lys Thr Arg Val Lys Tyr Pro Val Tyr Val Glu Ala
130                 135                 140

Tyr Ala Lys Leu Ser Asn Ser Thr Met Ala Ser Asp Val Trp Met Leu
145                 150                 155                 160

Ser Pro Asp Asp Thr Gln Glu Ile Asp Ile Glu Ala Tyr Gly Gly
                165                 170                 175

Asp Arg Asp Gly Gly Tyr Gly Ala Asp Arg Leu His Leu Ser His
            180                 185                 190

His Ile Phe Ile Arg Gln Pro Phe Lys Asp Tyr Gln Pro Lys Asp Ser
    195                 200                 205

Gly Ser Trp Tyr Lys Asp Asp Lys Gly Thr Leu Trp Arg Asp Asp Phe
    210                 215                 220

His Arg Val Gly Val Phe Trp Lys Asp Pro Phe Thr Leu Glu Tyr Tyr
225                 230                 235                 240

Val Asp Gly Glu Leu Val Arg Thr Ile Ser Gly Lys Asp Ile Ile Asp
                245                 250                 255

Pro Asn Asn Tyr Thr Gly Gly Thr Gly Leu Val Lys Asp Met Asp Ile
            260                 265                 270

Ile Ile Asn Met Glu Asp Gln Ser Trp Arg Ala Val Lys Gly Leu Ser
275                 280                 285

Pro Thr Asp Glu Glu Leu Lys Asn Val Glu Asp His Thr Phe Leu Val
    290                 295                 300

Asp Trp Ile Arg Val Tyr Thr Leu Val Pro Glu Glu
305                 310                 315

<210> SEQ ID NO 2
<211> LENGTH: 747
<212> TYPE: PRT
<213> ORGANISM: Unknown
<220> FEATURE:
<223> OTHER INFORMATION: Saccharophagus degradans exo-beta-agarase
      Aga50D

<400> SEQUENCE: 2

Met Leu Phe Asp Phe Glu Asn Asp Gln Val Pro Ser Asn Ile His Phe
1               5                   10                  15

Leu Asn Ala Arg Ala Ser Ile Glu Thr Tyr Thr Gly Ile Asn Gly Glu
            20                  25                  30

Pro Ser Lys Gly Leu Lys Leu Ala Met Gln Ser Lys Gln His Ser Tyr
        35                  40                  45

Thr Gly Leu Ala Ile Val Pro Glu Gln Pro Trp Asp Trp Ser Glu Phe
    50                  55                  60

Thr Ser Ala Ser Leu Tyr Phe Asp Ile Val Ser Val Gly Asp His Ser
65                  70                  75                  80

Thr Gln Phe Tyr Leu Asp Val Thr Asp Gln Asn Gly Ala Val Phe Thr
                85                  90                  95

Arg Ser Ile Asp Ile Pro Val Gly Lys Met Gln Ser Tyr Tyr Ala Lys
            100                 105                 110

Leu Ser Gly His Asp Leu Glu Val Pro Asp Ser Gly Asp Val Asn Asp
        115                 120                 125

Leu Asn Leu Ala Ser Gly Leu Arg Ser Asn Pro Pro Thr Trp Thr Ser
    130                 135                 140

Asp Asp Arg Gln Phe Val Trp Met Trp Gly Val Lys Asn Leu Asp Leu
145                 150                 155                 160
```

```
Ser Gly Ile Ala Lys Ile Ser Leu Ser Val Gln Ser Ala Met His Asp
            165                 170                 175

Lys Thr Val Ile Ile Asp Asn Ile Arg Ile Gln Pro Asn Pro Pro Gln
            180                 185                 190

Asp Glu Asn Phe Leu Val Gly Leu Val Asp Glu Phe Gly Gln Asn Ala
            195                 200                 205

Lys Val Asp Tyr Lys Gly Lys Ile His Ser Leu Glu Glu Leu His Ala
            210                 215                 220

Ala Arg Asp Val Glu Leu Ala Glu Leu Asp Gly Lys Pro Met Pro Ser
225                 230                 235                 240

Arg Ser Lys Phe Gly Gly Trp Leu Ala Gly Pro Lys Leu Lys Ala Thr
            245                 250                 255

Gly Tyr Phe Arg Thr Glu Lys Ile Asn Gly Lys Trp Met Leu Val Asp
            260                 265                 270

Pro Glu Gly Tyr Pro Tyr Phe Ala Thr Gly Leu Asp Ile Ile Arg Leu
            275                 280                 285

Ser Asn Ser Ser Thr Met Thr Gly Tyr Asp Tyr Asp Gln Ala Thr Val
            290                 295                 300

Ala Gln Arg Ser Ala Asp Asp Val Thr Pro Glu Asp Ser Lys Gly Leu
305                 310                 315                 320

Met Ala Val Ser Glu Lys Ser Phe Ala Thr Arg His Leu Ala Ser Pro
            325                 330                 335

Thr Arg Ala Ala Met Phe Asn Trp Leu Pro Asp Tyr Asp His Pro Leu
            340                 345                 350

Ala Asn His Tyr Asn Tyr Arg Arg Ser Ala His Ser Gly Pro Leu Lys
            355                 360                 365

Arg Gly Glu Ala Tyr Ser Phe Tyr Ser Ala Asn Leu Glu Arg Lys Tyr
            370                 375                 380

Gly Glu Thr Tyr Pro Gly Ser Tyr Leu Asp Lys Trp Arg Glu Val Thr
385                 390                 395                 400

Val Asp Arg Met Leu Asn Trp Gly Phe Thr Ser Leu Gly Asn Trp Thr
            405                 410                 415

Asp Pro Ala Tyr Tyr Asp Asn Asn Arg Ile Pro Phe Phe Ala Asn Gly
            420                 425                 430

Trp Val Ile Gly Asp Phe Lys Thr Val Ser Ser Gly Ala Asp Phe Trp
            435                 440                 445

Gly Ala Met Pro Asp Val Phe Asp Pro Glu Phe Lys Val Arg Ala Met
450                 455                 460

Glu Thr Ala Arg Val Val Ser Glu Glu Ile Lys Asn Ser Pro Trp Cys
465                 470                 475                 480

Val Gly Val Phe Ile Asp Asn Glu Lys Ser Phe Gly Arg Pro Asp Ser
            485                 490                 495

Asp Lys Ala Gln Tyr Gly Ile Pro Ile His Thr Leu Gly Arg Pro Ser
            500                 505                 510

Glu Gly Val Pro Thr Arg Gln Ala Phe Ser Lys Leu Lys Ala Lys
            515                 520                 525

Tyr Lys Thr Ile Ala Ala Leu Asn Asn Ala Trp Gly Leu Lys Leu Ser
            530                 535                 540

Ser Trp Ala Glu Phe Asp Leu Gly Val Asp Val Lys Ala Leu Pro Val
545                 550                 555                 560

Thr Asp Thr Leu Arg Ala Asp Tyr Ser Met Leu Leu Ser Ala Tyr Ala
            565                 570                 575
```

```
Asp Gln Tyr Phe Lys Val Val His Gly Ala Val Glu His Tyr Met Pro
            580                 585                 590

Asn His Leu Tyr Leu Gly Ala Arg Phe Pro Asp Trp Gly Met Pro Met
        595                 600                 605

Glu Val Val Lys Ala Ala Ala Lys Tyr Ala Asp Val Val Ser Tyr Asn
    610                 615                 620

Ser Tyr Lys Glu Gly Leu Pro Lys Gln Lys Trp Ala Phe Leu Ala Glu
625                 630                 635                 640

Leu Asp Lys Pro Ser Ile Ile Gly Glu Phe His Ile Gly Ala Met Asp
                645                 650                 655

His Gly Ser Tyr His Pro Gly Leu Ile His Ala Ala Ser Gln Ala Asp
            660                 665                 670

Arg Gly Glu Met Tyr Lys Asp Tyr Met Gln Ser Val Ile Asp Asn Pro
        675                 680                 685

Tyr Phe Val Gly Ala His Trp Phe Gln Tyr Met Asp Ser Pro Leu Thr
    690                 695                 700

Gly Arg Ala Tyr Asp Gly Glu Asn Tyr Asn Val Gly Phe Val Asp Val
705                 710                 715                 720

Thr Asp Thr Pro Tyr Gln Glu Met Val Asp Ala Ala Lys Glu Val Asn
                725                 730                 735

Ala Lys Ile Tyr Thr Glu Arg Leu Gly Ser Lys
            740                 745

<210> SEQ ID NO 3
<211> LENGTH: 368
<212> TYPE: PRT
<213> ORGANISM: Unknown
<220> FEATURE:
<223> OTHER INFORMATION: Saccharophagus degradans alpha-neoagarobiose
      hydrolase SdNABH

<400> SEQUENCE: 3

Met Ser Asp Ser Lys Val Asn Lys Lys Leu Ser Lys Ala Ser Leu Arg
1               5                   10                  15

Ala Ile Glu Arg Gly Tyr Asp Glu Lys Gly Pro Glu Trp Leu Phe Glu
            20                  25                  30

Phe Asp Ile Thr Pro Leu Lys Gly Asp Leu Ala Tyr Glu Glu Gly Val
        35                  40                  45

Ile Arg Arg Asp Pro Ser Ala Val Leu Lys Val Asp Asp Glu Tyr His
    50                  55                  60

Val Trp Tyr Thr Lys Gly Glu Gly Glu Thr Val Gly Phe Gly Ser Asp
65                  70                  75                  80

Asn Pro Glu Asp Lys Val Phe Pro Trp Asp Lys Thr Glu Val Trp His
                85                  90                  95

Ala Thr Ser Lys Asp Lys Ile Thr Trp Lys Glu Ile Gly Pro Ala Ile
            100                 105                 110

Gln Arg Gly Ala Ala Gly Ala Tyr Asp Asp Arg Ala Val Phe Thr Pro
        115                 120                 125

Glu Val Leu Arg His Asn Gly Thr Tyr Tyr Leu Val Tyr Gln Thr Val
    130                 135                 140

Lys Ala Pro Tyr Leu Asn Arg Ser Leu Glu His Ile Ala Ile Ala Tyr
145                 150                 155                 160

Ser Asp Ser Pro Phe Gly Pro Trp Thr Lys Ser Asp Ala Pro Ile Leu
                165                 170                 175

Ser Pro Glu Asn Asp Gly Val Trp Asp Thr Asp Glu Asp Asn Arg Phe
            180                 185                 190
```

```
Leu Val Lys Glu Lys Gly Ser Phe Asp Ser His Lys Val His Asp Pro
        195                 200                 205

Cys Leu Met Phe Phe Asn Asn Arg Phe Tyr Leu Tyr Tyr Lys Gly Glu
        210                 215                 220

Thr Met Gly Glu Ser Met Asn Met Gly Gly Arg Glu Ile Lys His Gly
225                 230                 235                 240

Val Ala Ile Ala Asp Ser Pro Leu Gly Pro Tyr Thr Lys Ser Glu Tyr
                245                 250                 255

Asn Pro Ile Thr Asn Ser Gly His Glu Val Ala Val Trp Pro Tyr Lys
                260                 265                 270

Gly Gly Met Ala Thr Met Leu Thr Thr Asp Gly Pro Glu Lys Asn Thr
            275                 280                 285

Cys Gln Trp Ala Glu Asp Gly Ile Asn Phe Asp Ile Met Ser His Ile
        290                 295                 300

Lys Gly Ala Pro Glu Ala Val Gly Phe Phe Arg Pro Glu Ser Asp Ser
305                 310                 315                 320

Asp Asp Pro Ile Ser Gly Ile Glu Trp Gly Leu Ser His Lys Tyr Asp
                325                 330                 335

Ala Ser Trp Asn Trp Asn Tyr Leu Cys Phe Phe Lys Thr Arg Arg Gln
            340                 345                 350

Val Leu Asp Ala Gly Ser Tyr Gln Gln Thr Gly Asp Ser Gly Ala Val
        355                 360                 365
```

<210> SEQ ID NO 4
<211> LENGTH: 951
<212> TYPE: DNA
<213> ORGANISM: Unknown
<220> FEATURE:
<223> OTHER INFORMATION: Bacteroides plebeius BpGH16A DNA sequence

<400> SEQUENCE: 4

```
atgaagagaa aactgtttac tatttgttta gcatcgttgc aatttgcatg tgcagcagaa        60
aatttaaata taaatcata  cgagtgggac atctatcctg taccagctaa tgctggtgac       120
ggtatggtgt ggaaacttca tccacagtcg gacgactta  attatattgc tgacgaaaag       180
gataaaggaa aagagttcta tgccaaatgg actgatttct atcataatca ttggacaggg       240
cctgctccta caatatggca gagagaccat gtttccgttt cagacggatt ccttaaaatc       300
agagccagcc gtcctgaaga tgtccctcta agaaagttg  taagcggacc taacacaaag       360
gaactcccgg gaacctatac aggatgtatt acatcgaaga ctcgtgtaaa atatccggtt       420
tatgtagaag catacgccaa actttcaaat tcaaccatgg catccgatgt atggatgctt       480
agccctgatg atactcagga atcgatatt  atagaggcat acgtggtga  tagagacggt       540
ggaggttatg gtgccgacag acttcactta agccatcaca tattcatccg tcagccattc       600
aaggattatc agccaaagga ttcaggttca tggtataagg atgacaaggg aacattgtgg       660
cgcgatgatt ttcatcgtgt tggagtattc tggaaagatc ctttcacact tgaatattat       720
gtagatggag aactcgtcag aactataagc ggtaaggata ttattgatcc caacaactac       780
actggtggca cggggttggt taaggatatg acatcataa  taaatatgga agaccaaagc       840
tggagggccg ttaaaggttt aagccctacg gatgaggaac tgaaaaatgt ggaagatcac       900
actttccttg tcgactggat aagggttat  acactggtcc cagaagaata g              951
```

<210> SEQ ID NO 5
<211> LENGTH: 2244

```
<212> TYPE: DNA
<213> ORGANISM: Unknown
<220> FEATURE:
<223> OTHER INFORMATION: Saccharophagus degradans Aga50D DNA sequence

<400> SEQUENCE: 5
atgttattcg attttgaaaa cgatcaagtc ccttcaaata ttcatttttt aaatgcgcgt      60
gcaagtatag aaacctatac cggtataaat ggcgagccga gtaaagggtt aaagttggcg     120
atgcagtcca agcagcacag ttatactggc cttgccattg tgccagagca gccttgggat     180
tggagcgagt ttacctctgc tagcttgtat ttcgatatag tcagtgttgg cgatcattcc     240
acacaatttt atttagatgt taccgaccaa aatggcgccg tgtttacccg cagtattgat     300
attccagtgg gtaaaatgca atcgtactac gccaagttaa gcggtcacga tttagaagtg     360
cccgatagtg gagacgttaa cgatttaaac ctcgcctctg gcttgcgttc taacccgcct     420
acatggacat ctgacgatag gcagtttgtt tggatgtggg gagtgaaaaa tttagatttg     480
tcgggcattg ctaaaatatc gctaagtgtg caaagcgcaa tgcacgataa aacagttatt     540
atcgataata ttcgtattca acccaacccg ccgcaagatg aaaacttcct tgtcggtttg     600
gtagacgagt ttggccaaaa cgccaaagtt gattacaagg gtaaaatcca tagtttagaa     660
gaattgcatg cagcgcgcga tgtggaactg gccgagcttg atggcaagcc aatgcctagt     720
cgctctaagt ttggcggttg gttggccggc cccaagctaa aagctacagg gtactttcgc     780
acagaaaaaa ttaacggtaa atggatgcta gtagacccag aagggtaccc ttactttgct     840
acgggtttag acattattcg cctatctaat tcatctacca tgactggtta cgattacgat     900
caagctactg ttgctcagcg ctctgccgac gatgtaacac ctgaagactc aaaaggttta     960
atggcagtga gcgaaaaatc atttgctacg cgccacctag catcgccaac acgagcggca    1020
atgtttaact ggttgccaga ttacgatcac cctctcgcaa atcattataa ctaccgtcgc    1080
tctgcgcatt ccggcccact gaaacgcggt gaagcctaca gcttctacag tgccaacctt    1140
gagcgtaaat acggtgaaac ttaccccggt tcttacttgg ataagtggcg cgaagtaacg    1200
gtagacagaa tgctaaactg gggctttacc tcgctaggca actggactga cccagcatat    1260
tacgacaaca atcgcatacc gtttttcgcg aatggttggg taataggggga ttttaaaacc    1320 gtatctagcg gtgcggattt tggggcgca atgccagatg tattcgaccc agaatttaaa    1380
gtgcgcgcta tggaaacggc acgcgtggtt tcagaagaaa ttaaaaatag cccttggtgc    1440
gtaggggtat ttatcgataa cgaaaaaagc ttcggtcgcc ccgattccga taaggcgcaa    1500
tacggtattc ccattcatac cctcggtcgc ccaagcgaag gtgtgcctac taggcaggcg    1560
tttagtaagc tgcttaaagc caaatacaaa actatagccg cgttaaacaa tgcctggggg    1620
ttaaagctta gttcttgggc tgagtttgat ttgggcgtag atgtaaaagc gctgccggta    1680
accgatactc tgcgcgcaga ttactcaatg ttactttcgg cctatgcgga ccaatatttt    1740
aaggtggtac acgcgcggt tgaacattac atgccgaacc acttgtattt aggcgcacgc    1800
tttcctgatt ggggaatgcc aatggaggta gtgaaagctg ccgcaaaata cgccgatgtg    1860
gttagctata attcctacaa agagggcttg cctaagcaga agtgggcttt tttagcagag    1920
ctagataagc cgagtataat cggtgagttt cacataggtg ctatgatca cggttcgtat    1980 cacccgcggtt taattcacgc tgcgtcgcag gccgatagag gtgaaatgta caagagttat    2040
atgcaatcgg taattgataa cccctacttc gtaggcgcgc actggttcca gtatatggat    2100
tcgccattaa cgggcagagc ttatgatggt gaaaactaca atgtgggttt tgtggatgtt    2160
```

```
accgacacgc cgtaccaaga aatggtggat gcagcaaaag aagtaaatgc gaaaatatac    2220
accgaaaggc taggcagcaa ataa                                          2244

<210> SEQ ID NO 6
<211> LENGTH: 1107
<212> TYPE: DNA
<213> ORGANISM: Unknown
<220> FEATURE:
<223> OTHER INFORMATION: Saccharophagus degradans SdNABH DNA sequence

<400> SEQUENCE: 6
atgagcgatt caaaagtaaa taaaaaattg agtaaagcta gcctgcgagc catagagcgc     60
ggctacgatg aaaaggggcc tgaatggctg tttgagtttg atattacccc actaaaaggc    120
gacttagcct acgaagaagg cgtaattcgt cgagaccccca gcgcagtatt aaaggtggac    180
gatgaatatc acgtttggta caccaagggc gaaggtgaaa cagtaggctt cggcagcgac    240 aacccccgaag acaaagtctt cccatgggat aaaacagaag tttggcacgc cacctctaaa    300
gataagatta cttggaaaga aattggccct gccatacaac gcggcgcagc tggggcatat    360
gatgaccgtg cagtgttcac ccccgaagtc ctgcgccata acggcaccta ctaccttgta    420
tatcaaacgg taaaagcgcc ctacttaaac cgatcgctag agcatatagc catcgcatac    480
agcgattccc cctttggccc atggaccaaa tccgatgcgc caatttttaag cccagaaaat    540 gacggcgttt gggatacgga cgaagacaat cgattttttag taaaagagaa aggcagtttc    600
gatagccaca aagtacacga ccccctgctta atgttttttta acaatcgttt ctacctgtat    660
tacaaaggcg agactatggg cgaaagcatg aacatgggcg gcagagaaat aaaacacggt    720
gtagccattg ccgactcgcc acttgggccc tacaccaaaa gcgaatacaa ccctattacc    780
aatagtggcc atgaagttgc cgtatggccc tacaaaggtg gaatggccac catgctaacc    840
accgacgggc cagaaaaaaa cacctgccag tgggcagaag acggcattaa ctttgacatt    900
atgtcgcata taaaaggcgc accagaagca gtaggttttt ttagaccaga aagcgatagc    960
gacgacccta taagcggcat tgaatggggg ctaagccaca agtacgacgc cagctggaac   1020
tggaactatc tatgcttttt taaaacgcgt cgacaagttt tagatgcagg tagctatcag   1080
caaacaggcg attccggagc agtataa                                      1107
```

METHOD FOR PRODUCTION OF SUGAR ALCOHOL FROM RED ALGAE

CROSS REFERENCE TO RELATED APPLICATIONS

This application is a National Stage of International Application No. PCT/KR2019/011509 filed Sep. 5, 2019, claiming priority based on Korean Patent Application No. 10-2018-0106552 filed Sep. 6, 2018, the entire disclosures of which are incorporated herein by reference.

TECHNICAL FIELD

The present invention relates to a method of chemically producing novel sugar alcohols, 3,6-anhydro-L-galactitol (L-AHGol) and agarobititol (ABol) which is a disaccharide having the L-AHGol as a reducing end, from marine algae.

BACKGROUND ART

The ocean has a unique environment different from land, such as high pressure, low temperature, low oxygen content, and a small amount of light. For this reason, unlike terrestrial organisms, marine organisms have their own unique characteristics. Among marine organisms, marine algae, unlike land plants, have very unique characteristics such as absorbing and preserving moisture well because they inhabit the ocean. Among marine algae, especially, agar, which is obtained from red algae, retains moisture to form a gel, and therefore, it has been widely used in the food and pharmaceutical industry. Agarose, which is a major polysaccharide constituting the agar, is a polymer consisting of 3,6-anhydro-L-galactose (L-AHG) and D-galactose alternately linked by an α-1,3-bond and a β-1,4-bond. In this case, L-AHG, which is a rare sugar that does not exist in terrestrial organisms, can be used as a cosmetic material due to having excellent whitening and moisturizing effects and is a multifunctional high value-added material with anti-inflammatory, anti-caries, and colon cancer prevention effects. Due to the functionality of L-AHG, many studies have been conducted to produce L-AHG from red algae for use as a high value-added material. In addition, agarobiose (AB) which is a disaccharide having L-AHG as a reducing end is known to have an excellent anti-inflammatory effect.

However, since L-AHG and AB are very unstable under conditions of high temperatures and acids, they are easily converted into 5-hydroxymethyl furfural and thus lose the functionality thereof.

Sugar alcohols generally refer to all types of sugars whose aldehyde group or ketone group is substituted with an alcohol group by adding hydrogen. Sugar alcohols have a variety of functions that natural sugars do not have and also have lower sweetness than natural sugars and a refreshing feeling. For this reason, various sugar alcohols such as sorbitol, xylitol, mannitol, and the like have been used as food additives, and maltitol, lactitol, erythritol, and the like are themselves treated as foods. In addition, sugar alcohols may be converted into useful chemicals through chemical and biological catalytic reactions. In this way, sugar alcohols are potential high value-added materials, and there is a need for production of novel sugar alcohols.

The inventors of the present invention have attempted to compensate for the disadvantages of L-AHG and AB and confirm multifunctionality by producing L-AHGol and ABol which are the sugar alcohols of L-AHG and AB.

RELATED-ART DOCUMENTS

Patent Documents

Korean Registered Patent No. 10-1864800 (2018May 30)

Non-Patent Documents (Non-Patent Document 1) H T Kim et al., Bioresour. Technol. (2012) 107: 301-306

(Non-Patent Document 2) H T Kim et al., Bioresour. Technol. (2013) 136: 582-587
(Non-Patent Document 3) C H Lee et al., Appl. Environ. Microbiol. (2014) 80: 5965-5973 (Non-Patent Document 4) C H Lee et al., Process Biochem. (2015) 50: 1629-1633

DISCLOSURE

Technical Problem

The present invention is directed to providing a method of producing a sugar alcohol from agarose or agar by acid hydrolysis and chemical reduction with a reductant.

The present invention is also directed to providing a method of producing a sugar alcohol from agarose or agar by enzymatic saccharification and chemical reduction with a reductant.

Technical Solution

One aspect of the present invention provides a method of producing one or more sugar alcohols of agarobititol (ABol) and 3,6-anhydro-L-galactitol (L-AHGol) from agarose or agar, which includes the steps of: (1) acid-hydrolyzing 5 to 30% (w/w) of agarose or agar based on dry weight, which is a substrate, using a strong acid with a concentration of 0.1 to 5% (w/v) at 80 to 140° C. for 5 minutes to 500 minutes to produce one or more sugars of agarobiose and 3,6-anhydro-L-galactose (L-AHG); and (2) treating the produced sugars with a reductant.

Another aspect of the present invention provides a method of producing 3,6-anhydro-L-galactitol (L-AHGol) from agarose or agar, which includes the steps of: (1) saccharifying agarose or agar, which is a substrate, using endo-β-agarase, exo-β-agarase, and neoagarobiose hydrolase to produce 3,6-anhydro-L-galactose (L-AHG); and (2) treating the produced L-AHG with a reductant to induce reduction.

The material to be finally produced in the present invention is a sugar alcohol derived from agarose or agar, which is referred to as agarobititol (ABol) or 3,6-anhydro-L-galactitol (L-AHGol). The two types of sugar alcohols are in the form in which agarobiose (AB) and 3,6-anhydro-L-galactose (L-AHG) are reduced with a reductant, respectively. The AB or L-AHG is produced from agar or agarose largely in three ways through previous studies described in the Related-Art Documents of the present invention. First, there is a method of hydrolyzing agarose or agar using a strong acid at high temperature, and this method has a problem of degraded L-AHG yield but is economical due to a relatively simple process. Second, there is a method of using a β-agarase system, and endo- and exo-β-agarase and neoagarobiose hydrolase are used. This method has a problem of a complex process caused by using various enzymes, but the use of the enzymes results in high yield. Third, there is a method of liquefying agarose or agar using an acid or chemical catalyst and then saccharifying the liquefied agarose or agar using various enzymes to produce L-AHG. This method also has a problem of a complex process caused by performing saccharification using β-agarases after the liquefaction process, like the second method, but results in high yield. Therefore, the present invention has been completed by producing AB and L-AHG using the methods and then reducing the products with a reductant to convert the products into ABol and L-AHGol.

In addition, the method of the present invention is largely divided into a step of hydrolysis or saccharification of agarose or agar and a reduction step, and the steps are characterized in that they are performed simultaneously in a single reactor, and the specific reaction conditions of each step may vary.

In the method of the present invention, which uses acid hydrolysis, when agarose or agar is treated with a strong acid, the strong acid with a concentration of 0.1 to 5% (w/v), and specifically, 0.5 to 3% (w/v), may be used. Within the above-described concentration range, the production of 5-HMF caused by treatment of agarose or agar with a strong acid can be minimized, and simultaneously, a high concentration of AB can be produced, resulting in the production of L-AHG with high yield.

In addition, the treatment of agarose or agar with a strong acid may be performed using a strong acid with a concentration of 0.1 to 5% (w/v) at 80 to 140° C. for 5 minutes to 300 minutes. Specifically, the treatment may be performed using a strong acid with a concentration of 2% (w/v) at 90° C. for 5 minutes to 300 minutes, and, under the above-described conditions, most of the agarose or agar may be acid-hydrolyzed to produce AB.

Furthermore, to further hydrolyze the AB to produce L-AHG, more intensive reaction conditions are required. Specifically, the reaction may be performed using a strong acid with a concentration of 2% (w/v) at 120° C. for 10 minutes to 30 minutes.

The strong acid may be phosphoric acid, sulfuric acid, hydrochloric acid, nitric acid, or the like. More specifically, phosphoric acid may be used.

The amount of agarose or agar used in the treatment with the strong acid may be 5 to 20% (w/v), and more specifically, 10% (w/w) based on dry weight. Within the above-described content range, a liquefaction rate of 90%, 95%, or 98% or more may be achieved. Outside of the above-described content range, the hydrolysis rate of a substrate may be substantially degraded.

In the method of producing L-AHG from agarose or agar according to another embodiment of the present invention, agarose or agar may be directly saccharified into L-AHG, without passing through AB, using endo-β-agarase, exo-β-agarase, and neoagarobiose hydrolase, and this enzymatic method may increase the production yield of L-AHG compared to the acid hydrolysis method.

The endo-β-agarase, exo-β-agarase, and neoagarobiose hydrolase may be represented by amino acid sequences set forth in SEQ ID NO: 1, SEQ ID NO: 2, and SEQ ID NO: 3, respectively.

The endo-β-agarase, exo-β-agarase, and neoagarobiose hydrolase may be transcribed and translated through a DNA segment, that is, a coding gene involved in producing a polypeptide, having an intervening sequence between individual coding segments as well as regions before and after the coding region of the enzyme. For example, each enzyme may be transcribed and translated from base sequences set forth in SEQ ID NO: 4, SEQ ID NO: 5, and SEQ ID NO: 6, but the present invention is not limited thereto. In addition, one or more mutant proteins of the enzymes by transition, deletion, transposition, addition, and the like, which have hydrolysis activity with respect to the agarobiose, are also encompassed in the scope of the present invention for an enzyme, and preferably, an amino acid sequence having a sequence identity of 80% or more, 85% or more, 90% or more, 93% or more, 94% or more, 95% or more, 96% or more, 97% or more, 98% or more, or 99% or more with amino acid sequences set forth in SEQ ID NOS: 1 to 3 is included.

The endo-β-agarase may be derived from *Bacteroides plebeius*, and the exo-β-agarase and the neoagarobiose hydrolase may be derived from *Saccharophagus degradans* 2-40$^T$, but the present invention is not limited thereto.

The endo-β-agarase, exo-β-agarase, and neoagarobiose hydrolase may be isolated from cell lysates or supernatants of *Bacteroides plebeius* and *Saccharophagus degradans* 2-40$^T$ and purified and may also be produced and isolated by strains other than the above strains or artificial chemical synthesis using a genetic engineering recombination technique. In the case of using the recombination technique, the lysate or culture medium of transformed *E. coli* may be used as an alternative, but the present invention is not limited thereto. According to an embodiment, the enzymes may be obtained from *E. coli* transformed with recombinant vectors including base sequences set forth in SEQ ID NO: 4, SEQ ID NO: 5, and SEQ ID NO: 6, or a culture medium thereof.

The reaction of agar or agarose with endo-β-agarase, exo-β-agarase, and neoagarobiose hydrolase may be sequentially performed. Specifically, the reaction of agar or agarose, which is a substrate, with endo-β-agarase may be performed at 40 to 60° C. for 5 hours to 48 hours. More specifically, the reaction may be performed at 50° C. for 6 hours. Then, the reaction of the resulting product, which is a substrate, with exo-D-agarase may be performed at 20 to 40° C. for 1 hour to 10 hours. More specifically the reaction may be performed at 30° C. for 2 hours. Then, the reaction of the resulting product, which is a substrate, with neoagarobiose hydrolase may be performed at 20 to 40° C. for 1 hour to 10 hours. More specifically, the reaction may be performed at 30° C. for 2 hours.

As used herein, the terms "enzyme", "protein", and "polypeptide" are used interchangeably.

In the present invention, the fact that polypeptide has a specific ratio (e.g., 80%, 85%, 90%, 95%, or 99%) of sequence identity with another sequence means that when the two sequences are aligned and compared, the above-described ratio of amino acid residues are identical. The alignment and percent homology or identity may be determined using any suitable software program known in the art, for example, those described in the document [CURRENT PROTOCOLS IN MOLECULAR BIOLOGY (F. M. Ausubel et al. (eds) 1987 Supplement 30 section 7.7.18)]. As desirable programs, the GCG Pileup program, FASTA (Pearson et al.

1988 *Proc. Natl Acad. Sci* USA 85: 2444-2448), and BLAST (BLAST Manual, Altschul et al., Natl. Cent. Biotechnol. Inf., Natl Lib. Med. (NCIB NLM NIH), Bethesda, Md., and Altschul et al. 1997 NAR25: 3389-3402) may be used. As another desirable alignment program, ALIGN Plus (Scientific and Educational Software, PA) may be used, and preferably, a basic parameter may be used. As another available sequence software program, TFASTA Data Searching Program (Sequence Software Package Version 6.0, Genetics Computer Group, University of Wisconsin, Madison, Wis.) may be used.

As used herein, the term "recombination", when used in relation to a cell, nucleic acid, protein, or vector, means that the cell, nucleic acid, protein, or vector is modified by the introduction of a heterologous nucleic acid or protein or the alteration of the original nucleic acid or protein, or that the cell is derived from the modified cell. That is, for example, a recombinant cell expresses a gene that is not found in the original (non-recombinant) form of the cell, or otherwise expresses an original gene that is abnormally expressed or not expressed at all.

As used herein, the term "nucleic acid" encompasses single-stranded or double-stranded DNA, RNA, and chemical modifications thereof. "Nucleic acid" and "polynucleotide" may be used interchangeably herein. Since the genetic code is degenerated, one or more codons may be used to encode a specific amino acid, and polynucleotides encoding a specific amino acid sequence are encompassed in the present invention.

The term "introduction" for inserting a nucleic acid sequence into a cell means "transfection", "transformation", or "transduction" and encompasses the integration of a nucleic acid sequence into a eukaryotic or prokaryotic cell. In this case, the nucleic acid sequence is integrated into the genome of the cell (e.g., chromosome, plasmid, plastid, or mitochondrial DNA) and thus converted into an autonomous replicon or transiently expressed.

In the present invention, the step of reducing one or more sugars of agarobiose and 3,6-anhydro-L-galactose (L-AHG) with a reductant may be performed at the same time as or in the middle of the step of acid-hydrolyzing or enzymatically saccharifying agar or agarose, or at the time the step is terminated. According to a specific embodiment, when reduction is performed with a reductant at the terminal time the final product is sufficiently produced by performing acid hydrolysis or enzymatic saccharification of agar or agarose, the final product is produced with excellent yield.

Examples of the reductant include morpholine borane, piperidine borane, pyridine borane, piperazine borane, 2,6-lutidine borane, N,N-diethylaniline borane, 4-methylmorpholine borane (MMB), 1,4-oxathiane borane, ammonium, alkali and alkaline earth metal borohydrides, hypophosphites, sulfites, bisulfites, hydrosulfites, metabisulfites, dithionates, tetrathionates, thiosulfates, thioureas, hydrazines, hydroxylamines, aldehydes (including formaldehyde and glyoxal], glyoxylic acid, reducing sugars, and a combination thereof, but the present invention is not limited thereto. According to a specific embodiment, the reductant of the present invention may be 4-methylmorpholine borane (MMB), sodium borohydride, and a combination thereof.

Advantageous Effects

According to the present invention, optimal conditions that allow a sugar alcohol, which is a novel biomaterial, to be mass-produced from agarose or agar are established, particularly, agarose or agar can be easily and efficiently converted into a sugar alcohol by chemical reduction with a reductant, and a process of producing a sugar alcohol of the present invention is simplified by simultaneously performing acid hydrolysis and reduction in a single reactor.

DESCRIPTION OF DRAWINGS

FIGS. 1A-1E show results of agarobititol (ABol) and 3,6-anhydro-L-galactitol (L-AHGol) produced by reducing each of agarobiose (AB) and 3,6-anhydro-L-galactose (L-AHG) using 4-methylmorpholine borane (MMB) and sodium borohydride as reductants. FIG. 1A shows a high-performance liquid chromatography (HPLC) result. FIG. 1B shows the structural mechanism of conversion of AB into ABol and the molecular weight of AB and ABol. FIG. 1C shows a tandem mass spectrum of ABol as analyzed by LC/MS-IT-TOF, and an inserted diagram of FIG. 1C shows a mass spectrum of ABol. FIG. 1D shows the structural mechanism of conversion of L-AHG into L-AHGol and the molecular weight of L-AHG and L-AHGol. FIG. 1E shows a mass spectrum of L-AHGol as analyzed by LC/MS-IT-TOF.

FIG. 2 is a schematic diagram of production of ABol from agarose according to the present invention. ABol is produced from agarose by acid hydrolysis and reduction in a single reactor.

FIGS. 3A-3D show HPLC results of ABol produced according to the timing of addition of a reductant during acid hydrolysis for producing ABol from agarose in a single reactor. FIG. 3A shows a result of performing acid hydrolysis after the addition of a reductant at the beginning stage (0 hour), FIG. 3B shows a result of simultaneously performing acid hydrolysis and reduction by adding a reductant after 30 minutes of the acid hydrolysis, FIG. 3C shows a result of finally adding a reductant after as much AB as possible is produced by acid hydrolysis, and FIG. 3D shows a result of dividedly adding one third of a reductant at the beginning (0 mins), middle (150 mins), and final (240 mins) stages of acid hydrolysis.

FIG. 4 shows a HPLC result of ABol, which is separated from agarose hydrolysate containing ABol produced by the above method using activated charcoal and purified, according to each fraction.

FIG. 5 is a schematic diagram of production of L-AHGol from agarose according to the present invention. A of FIG. 5 is a diagram of production of L-AHGol by producing L-AHG from agarose only by acid hydrolysis and then reducing the produced L-AHG. B of FIG. 5 is a diagram of production of L-AHGol by producing L-AHG from agarose using a β-agarase system and then reducing the produced L-AHG.

FIG. 6A shows a result of L-AHGol produced from agarose by acid hydrolysis. FIG. 6B shows a thin layer chromatography (TLC) result of L-AHG produced from agarose using a β-agarase system. FIG. 6C shows a HPLC result of L-AHGol produced by reducing L-AHG obtained using a β-agarase system.

MODES OF THE INVENTION

Hereinafter, the present invention will be described in more detail with reference to examples according to the present invention, and the scope of the present invention is not limited to the following examples.

<Example 1> Conversion of AB and L-AHG into ABol and L-AHGol, respectively, using reductant To produce ABol and L-AHGol which are novel sugar alcohols corresponding to AB and L-AHG, respectively, the possibility of converting sugars into sugar alcohols using a reductant was examined (FIGS. 1A-1E). As a reductant for chemical reduction, 4-methylmorpholine borane (MMB) or sodium borohydride was used. High-performance liquid chromatography (HPLC) conditions included: column: HPX-87H, flow rate: 0.5 mL/min, and mobile phase: 0.005 M H2SO4. As a result, as shown in FIG. 1A, as AB and L-AHG were converted into sugar alcohols, the HPLC retention time thereof were slightly pushed back. To confirm the produced sugar alcohols, analysis was performed by LC/MS-IT-TOF.

Example 2 Confirmation of ABol and L-AHGol by Liquid Chromatography Hybrid Ion Trap Time-of-Flight Mass Spectrometry (LC/MS-IT-TOF) Analysis LC/MS-IT-TOF was used to analyze ABol and L-AHGol. As a column, a Hypercarb porous graphitic carbon LC column (100×2.1 mm, packed with 3 µm particles) was used, and the temperature of the LC column was maintained at 70° C. during analysis. A mobile phase consisted of 25 µM lithium chloride and acetonitrile and had a gradient of 0 to 80% during analysis at a flow rate of 0.2 mL/min for 41 minutes. Electrospray ionization was performed in a positive ion mode, and source-dependent parameters were set as follows: nebulizing gas flow: 1.5 L/min, interface voltage: 4.5 kV, detector voltage: 1.65 kV, curved desolvation line (CDL), and heat block temperature: 200° C. Mass spectrometry was performed in a range of 100 to 700 m/z.

When AB was reduced and thus converted into ABol, the molecular weight of ABol was 326 as shown in FIG. 1B. In this case, a lithium ion was added to ABol, and thus the finally analyzed molecular weight was 333. As shown in FIG. 1C, the main peak of ABol was exhibited at 333.2397. Also, as a result of confirming the chemical structure of ABol by the tandem mass spectrum, it can be seen that peaks at 171.1330 which is a molecular weight of L-AHGol having a lithium ion added thereto and 169.1192 which is a molecular weight of galactose excluding a water molecule and having a lithium ion added thereto were exhibited, indicating that ABol consisted of L-AHGol and galactose.

L-AHGol was also analyzed by LC/MS-IT-TOF. As shown in FIG. 1D, when L-AHG was reduced and thus converted into L-AHGol, the molecular weight was changed from 162 to 164, and when a lithium ion was added, a molecular weight of 171 was exhibited. As shown in FIG. 1E, as a result of analyzing L-AHGol, it was confirmed that peaks at 171.1431 and 335.2595 which is a molecule weight of two L-AHGol molecules having a lithium ion added thereto, indicating that ABol was hydrolyzed to produce L-AHGol.

Example 3 Production of ABol by Acid Hydrolysis and Reduction in Single Reactor To produce ABol by acid hydrolysis and reduction in a single reactor, ABol was produced by varying the timing of addition of a reductant during acid hydrolysis of agarose. Common reaction conditions were as follows. For acid hydrolysis, 10% (w/w) of agarose was used as a substrate, and the reaction was performed using 2% (w/v) phosphoric acid at 90° C. In this case, Rezex ROA-Organic Acid was used as a HPLC column, a mobile phase was 0.005 M $H_2SO_4$, and a flow rate was 0.6 mL/min.

As shown in FIGS. 3A-3D, ABol was produced by varying the timing of addition of a reductant in four ways during acid hydrolysis of agarose. In this case, as the reductant, 0.45 M MMB was used. According to the first condition, the reductant was added before acid hydrolysis of agarose (0 hour) (FIG. 3A). As a result, although ABol was produced over time, the amount and yield of finally produced ABol were 3.2 g/L and about 3.1%, respectively, which were very small as compared to the amount of used agarose. This is because the addition of the reductant, which is a strong alkali, at the beginning stage resulted in an increase in pH, and thus a hydrolysis effect caused by phosphoric acid was reduced, and agarose was hardly hydrolyzed under this condition. According to the second condition, the reductant was added after agarose was somewhat liquefied by acid hydrolysis, and then acid hydrolysis and reduction were simultaneously performed (FIG. 3B). Under this condition, the reductant was added after 30 minutes of acid hydrolysis. As a result, AB was produced before the addition of the reductant and converted into ABol after the addition of the reductant, and thus the graph corresponding to AB disappeared. Afterward, although the amount of ABol increased over time (18.8 g/L was produced after 30 minutes, and about 27.5 g/L was finally produced), ABol was finally produced with a low yield of 26.3%. This is also because, although agarose was liquefied by acid hydrolysis at the beginning stage, the addition of the reductant resulted in a reduction of the hydrolysis effect caused by phosphoric acid. According to the third condition, after AB was sufficiently produced from agarose by acid hydrolysis, the reductant was added at the final stage so as to convert the AB into ABol (FIG. 3C). Under this condition, AB was predominantly produced over time, and the reductant was added at the time the AB was no longer produced. As a result, 88.6 g/L of ABol was finally produced, and thus a very high ABol yield of about 85.2% was achieved. However, under this condition, the produced AB was excessively hydrolyzed to produce galactose, L-AHGol, and a small amount of 5-HMF. Finally, according to the fourth condition, the reductant was dividedly added by thirds to prevent production of the products resulting from excessive hydrolysis (FIG. 3D). The reductant was dividedly added before acid hydrolysis (0 hour), when AB was produced (150 mins), and at the final stage (240 mins). As a result, the amount of ABol produced during the first 30 minutes was 17.4 g/L, which was larger than that when the reductant was added at the beginning stage (first condition). Afterward, 42.9 g/L of ABol was produced after 150 minutes, and 55.4 g/L of ABol was finally produced. Under this condition, although 5-HMF, which is the product resulting from excessive hydrolysis, was not produced, a low final ABol yield of 53.4% was achieved compared to the third condition.

TABLE 1

| The stage for the addition of reductant | Titer (g/L) | Yield (%, w/w) |
| --- | --- | --- |
| At the beginning stage | 3.2 | 3.1 |
| At the middle stage | 27.4 | 26.3 |
| At the final stage | 88.6 | 85.2 |
| Pulse feeding | 55.5 | 53.4 |

Example 4 Separation and Purification of ABol Using Activated Charcoal

To selectively separate ABol from agarose hydrolysate containing a large amount of ABol obtained by acid-hydrolyzing agarose and reducing the resulting product with a reductant as described above and purify the ABol, activated charcoal was used. A ratio of a substrate and activated charcoal was set to 1:50. For example, 5 g of activated charcoal was used per 100 mg of agarose which is a substrate. Before being used, the activated charcoal was washed with distilled water several times. Afterward, agarose hydrolysate containing ABol produced by acid hydrolysis and reduction was allowed to be adsorbed onto the activated charcoal while stirring for about 10 minutes. Then, centrifugation was performed at 10,000 rpm for 10 minutes to analyze a supernatant containing unadsorbed components.

As a result, as shown in FIG. 4, the phosphoric acid and MMB used for acid hydrolysis and reduction were not adsorbed onto activated charcoal and thus contained in the supernatant, and high DP of sugars and sugar alcohols, including ABol, were adsorbed onto activated charcoal. The supernatant was removed to eliminate the acid and reductant, and washing with distilled water was performed again. Afterward, ABol was selectively separated from activated charcoal and purified using 20% (v/v) ethanol.

Example 5 Production of L-AHGol From Agarose

To produce L-AHGol from agarose, two ways were used as shown in FIG. 5. First, as shown in FIG. 5A, L-AHG was directly produced from agarose using an acid and then finally reduced to produce L-AHGol. In this case, more intensive conditions than the above-described conditions for producing AB from agarose were applied. Specifically, 10% (w/v) of agarose was allowed to react with phosphoric acid with a concentration of 2% (w/v) at 120° C. for 20 minutes. Afterward, L-AHG was reduced using 0.45 M sodium borohydride as a reductant to produce L-AHGol. In this case, HPLC analysis conditions included: column: HPX-87H, flow rate: 0.5 mL/min, mobile phase: 0.005 M $H_2SO_4$. In this way, since acid hydrolysis was performed under more intensive conditions, L-AHG was excessively hydrolyzed to produce a large amount of 5-HMF. Therefore, the amount of finally produced L-AHGol was very small. Also, since AB was not completely hydrolyzed into L-AHG and galactose which are monosaccharides, a considerable amount of ABol was also produced (FIG. 6A).

Second, a β-agarase system was used to produce a higher yield of L-AHG from agarose (FIG. 5B). Enzymes used in this way were endo-type β-agarase BpGH16A derived from *Bacteroides plebeius* DSM 17135, exo-type β-agarase Aga50D derived from *Saccharophagus degradans* 2-40$^T$, and neoagarobiose hydrolase SdNABH. Each of the genes represented by base sequences set forth in SEQ ID NOS: 4 to 6, which encode the enzymes, was introduced into *E. coli* BL21(DE3) using a pET21α vector. To obtain recombinant proteins, cells were allowed to grow in 100 μg/mL of an ampicillin-containing LB medium at 37° C. until the exponential growth phase (OD 0.4~0.6), 0.1 mM isopropyl-β-di-thiogalactopyranoside (IPTG) was added, and recombinant proteins were overexpressed at 16° C. for 16 hours. Then, the cell culture medium was centrifuged at 4° C. and 10,000 rpm for 20 minutes, and cells were recovered. To obtain the intracellular recombinant protein, the cells were released with a buffer solution (20 mM Tris-HCl, pH 7.4) and then lyzed using an ultrasonic device. Centrifugation was performed at 4° C. and 16,000 rpm for 20 minutes, and then proteins were isolated and purified using a HisTrap column (GE Healthcare). The recombinant proteins thus obtained were used to produce L-AHG.

An agarose substrate was allowed to react with a BpGH16A enzyme in a 20 mM Tris-HCl buffer (pH 7.0) at 50° C. for 6 hours. Afterward, as a substrate, neoagarooligosaccharide, which was a product of the BpGH16A reaction, was allowed to react with Aga50D at 30° C. for 2 hours. Finally, a product of the Aga50D reaction was allowed to react with SdNABH at 30° C. for 2 hours to produce L-AHG and galactose (FIG. 6B). In addition, the enzymatic hydrolysate of agarose was finally treated with 0.45 M sodium borohydride as a reductant to convert L-AHG into L-AHGol (FIG. 6C). When the β-agarase system was used, since L-AHG was directly produced from agarose without producing agarobiose, L-AHGol was finally produced as a final product of the reductant treatment, and Galol was produced as a by-product.

The invention claimed is:

1. A method of producing a sugar alcohol selected from the group consisting of agarobititol (ABol) and 3,6-anhydro-L-galactitol (L-AHGol) from agarose or agar, the method comprising the steps of:
   (1) acid-hydrolyzing 5 to 30% (w/w) based on dry weight of agarose or agar, which is a substrate, using a strong acid with a concentration of 0.1 to 5% (w/v) at 80 to 140° C. for 5 minutes to 500 minutes to produce a sugar selected from the group consisting of agarobiose and 3,6-anhydro-L-galactose (L-AHG); and
   (2) treating the produced sugars with a reductant selected from the group consisting of 4-methylmorpholine borane (MMB) and sodium borohydride,
   wherein all the steps are performed in a single reactor, and
   wherein the reductant treatment of step (2) is performed at the time the acid hydrolysis of step (1) is terminated.

2. A method of producing 3,6-anhydro-L-galactitol (L-AHGol) from agarose or agar, the method comprising the steps of:
   (1) saccharifying agarose or agar, which is a substrate, using endo-β-agarase, exo-β-agarase, and neoagarobiose hydrolase to produce 3,6-anhydro-L-galactose (L-AHG); and
   (2) treating the produced 3,6-anhydro-L-galactose (L-AHG) with a reductant selected from the group consisting of 4-methylmorpholine borane (MMB) and sodium borohydride,
   wherein all the steps are performed in a single reactor, and
   wherein the reductant treatment of step (2) is performed at the time the saccharification of step (1) is terminated.

3. The method of claim 2, wherein the endo-β-agarase is the amino acid sequence set forth in SEQ ID NO: 1, the exo-β-agarase is the amino acid sequence set forth in SEQ ID NO: 2 and the neoagarobiose hydrolase is the amino acid sequence set forth in SEQ ID NO: 3.

* * * * *